US011771810B2

(12) United States Patent
Silvestri et al.

(10) Patent No.: US 11,771,810 B2
(45) Date of Patent: Oct. 3, 2023

(54) OXYGENATOR WITH THERMAL INSULATION

(71) Applicant: Sorin Group Italia S.r.l., Mirandola (IT)

(72) Inventors: Claudio Silvestri, Mirandola (IT); Clara Pandolfini, Roverbella (IT); Barbara Lancini, Milan (IT)

(73) Assignee: Sorin Group Italia S.r.l., Mirandola (IT)

( * ) Notice: Subject to any disclaimer, the term of this patent is extended or adjusted under 35 U.S.C. 154(b) by 909 days.

(21) Appl. No.: 16/612,211

(22) PCT Filed: Jun. 1, 2017

(86) PCT No.: PCT/IB2017/053229
§ 371 (c)(1),
(2) Date: Nov. 8, 2019

(87) PCT Pub. No.: WO2018/220427
PCT Pub. Date: Dec. 6, 2018

(65) Prior Publication Data
US 2021/0077701 A1 Mar. 18, 2021

(51) Int. Cl.
*A61M 1/16* (2006.01)
*A61M 39/20* (2006.01)

(52) U.S. Cl.
CPC .......... *A61M 1/1698* (2013.01); *A61M 39/20* (2013.01); *A61M 2205/366* (2013.01); *A61M 2205/3633* (2013.01)

(58) Field of Classification Search
CPC ................ A61M 1/1698; A61M 39/20; A61M 2205/3633; A61M 2205/366
See application file for complete search history.

(56) References Cited

U.S. PATENT DOCUMENTS

| 3,927,981 A | 12/1975 | Viannay et al. |
| 4,948,560 A * | 8/1990 | Deguchi ............. A61M 1/1698 210/321.89 |
| 5,817,279 A * | 10/1998 | Eilers .................. A61M 1/1698 422/46 |

FOREIGN PATENT DOCUMENTS

| DE | 3142751 A1 | 6/1982 |
| EP | 0183250 A2 | 6/1986 |
| EP | 2543403 A2 | 1/2013 |

(Continued)

OTHER PUBLICATIONS

International Search Report and Written Opinion received for PCT Patent Application No. PCT/IB2017/053229, dated Jan. 30, 2018, 11 pages.

(Continued)

*Primary Examiner* — Benjamin J Klein
(74) *Attorney, Agent, or Firm* — Seager, Tufte & Wickhem LLP

(57) ABSTRACT

An oxygenator includes a housing having a blood inlet and a blood outlet, the blood inlet extending into an interior of the housing. A heat exchanger is disposed within the housing, and is coupled, at an inlet end, to a heat-exchange fluid inlet. A gas exchanger also is disposed within the housing, and includes a bundle of gas-exchange fibers coupled, at a gas outlet end, to a gas-exchange fluid outlet. The oxygenator includes at least one insulator configured to thermally insulate at least the gas outlet end of the bundle of gas-exchange fibers.

19 Claims, 5 Drawing Sheets

(56) References Cited

FOREIGN PATENT DOCUMENTS

| JP | S61128978 A | 6/1986 |
| JP | H0814074 A | 6/1996 |
| JP | 2012135434 A | 7/2012 |
| JP | 2015-039478 A | 3/2015 |
| JP | 2015039478 A | 3/2015 |

OTHER PUBLICATIONS

International Search Report dated Jan. 30, 2018 for International Application No. PCT/IB2017/053229.

* cited by examiner

OXYGENATOR WITH THERMAL INSULATION

TECHNICAL FIELD

The present disclosure relates to medical devices and methods for processing blood in extracorporeal circulation. More specifically, the disclosure relates to oxygenators.

BACKGROUND

Blood perfusion entails encouraging blood through the vessels of the body. For such purposes, blood perfusion systems typically entail the use of one or more pumps in an extracorporeal circuit that is interconnected with the vascular system of a patient. Cardiopulmonary bypass surgery typically requires a perfusion system that provides for the temporary cessation of the heart to create a still operating field by replacing the function of the heart and lungs. Such isolation allows for the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures oxygen-poor blood, i.e., venous blood, is gravity-drained or vacuum suctioned from a large vein entering the heart or other veins in the body (e.g., femoral) and is transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is filtered and then returned through an arterial line to the aorta, femoral artery, or other artery.

During the use of any oxygenator, vapor condensation may occur within the gas-exchange fibers of the oxygenator. When this occurs, it may be evidenced by a progressive decrease of gas exchange performances. Conventionally, in order to recover normal functionality, the perfusionist manually removes the condensed water from the gas exchanger. This is not often easy to do. Therefore, it is desirable to reduce and/or prevent vapor condensation.

SUMMARY

Embodiments of the subject matter disclosed herein include an oxygenator comprising a housing having a blood inlet and a blood outlet, the blood inlet extending into an interior of the housing; a heat exchanger disposed within the housing, the heat exchanger coupled, at an inlet end to a heat-exchange fluid inlet; a gas exchanger disposed within the housing, the gas exchanger comprising a bundle of gas-exchange fibers coupled, at a gas outlet end, to a gas-exchange fluid outlet; and at least one insulator configured to thermally insulate at least the gas outlet end of the bundle of gas-exchange fibers. In embodiments, the at least one insulator comprises an insulating material and/or an insulating chamber. In embodiments, the at least one insulator includes an insulating material, wherein the insulating material is transparent (e.g., a transparent paint, coating, adhesive tape, etc.). In embodiments, the at least one insulator includes an insulating chamber, wherein the insulating chamber is configured to receive an insulating fluid. The insulating fluid may comprise a portion of a flow of heat-exchange fluid being provided to the oxygenator. In embodiments, a conduit is disposed outside of the oxygenator housing and configured to provide the insulating fluid to the insulating chamber. In embodiments, the insulating chamber surrounds at least a portion of the housing.

In embodiments, the oxygenator includes a first end cap disposed at a first end of the housing, and a second end cap disposed at a second end of the housing, wherein the insulating chamber is partially defined between an outer surface of the second end of the housing and an inner surface of the second end cap. In embodiments, the insulating chamber is at least partially defined by a channel defined in an inner surface of the second end cap. In embodiments, the oxygenator further includes a connecting channel defined in the inner surface of the second end cap, the connecting channel extending between a heat-exchange fluid inlet channel and the insulating chamber. In embodiments, the oxygenator further includes an additional connecting channel defined in the inner surface of the second end cap, the additional connecting channel extending between the insulating chamber and a heat-exchange fluid outlet channel. The connecting channel and additional connecting channel may be offset from one another.

Embodiments of the subject matter disclosed herein include an oxygenator comprising a housing having a blood inlet and a blood outlet, the blood inlet extending into an interior of the housing; a heat exchanger disposed within the housing, the heat exchanger coupled, at an inlet end to a heat-exchange fluid inlet; a gas exchanger disposed within the housing, the gas exchanger coupled, at a gas outlet end, to a gas-exchange fluid outlet; and an insulating chamber configured to receive an insulating fluid to thermally insulate at least the gas outlet end of the bundle of gas-exchange fibers. According to embodiments, the oxygenator includes an insulating material disposed on an outer surface of the housing (e.g., a transparent paint, coating, adhesive tape, etc.). In embodiments, the insulating chamber surrounds at least a portion of the housing. In embodiments, the oxygenator further includes a first end cap disposed at a first end of the housing, and a second end cap disposed at a second end of the housing, wherein the insulating chamber is bounded by an outer surface of the second end of the housing, an inner surface of a flange extending from the housing, and an inner surface of the second end cap. In embodiments, the insulating chamber comprises an at least partially annular chamber extending at least partially around the gas outlet end of the gas exchanger. In embodiments, the insulating fluid comprises a portion of a flow of heat-exchange fluid being provided to the oxygenator.

Embodiments of the subject matter disclosed herein include an oxygenator comprising a housing having a blood inlet and a blood outlet, the blood inlet extending into an interior of the housing; a first end cap disposed at a first end of the housing; a second end cap disposed at a second end of the housing, wherein the insulating chamber is partially defined between an outer surface of the second end of the housing and an inner surface of the second end cap; a heat exchanger disposed within the housing, the heat exchanger coupled, at an inlet end, to a heat-exchange fluid inlet; a gas exchanger disposed within the housing, the gas exchanger comprising a bundle of gas-exchange fibers coupled, at a gas outlet end, to a gas-exchange fluid outlet; and an insulating chamber configured to receive an insulating fluid to thermally insulate at least the gas outlet end of the bundle of gas-exchange fibers, wherein the insulating chamber is at least partially defined by a channel defined in an inner surface of the second end cap.

While multiple embodiments are disclosed, still other embodiments of the present disclosure will become apparent to those skilled in the art from the following detailed description, which shows and describes illustrative embodiments of the disclosed subject matter. Accordingly, the drawings and detailed description are to be regarded as illustrative in nature and not restrictive.

Figure 1:
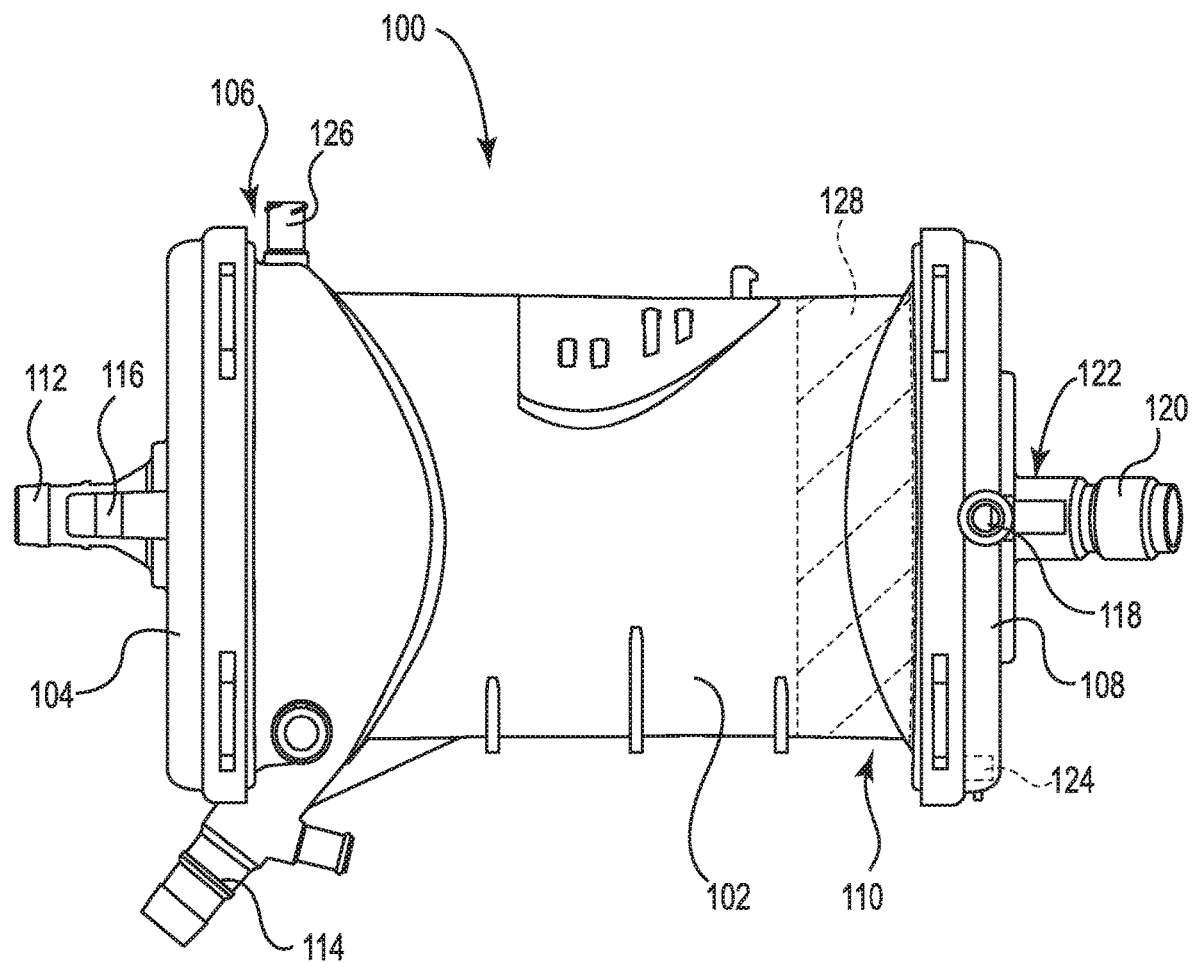
FIG. 1 is a schematic diagram of an illustrative oxygenator, in accordance with embodiments of the disclosed subject matter.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

In hollow fiber oxygenators, blood is circulated outside the fibers, while gas flows inside. Gas temperature within most of the oxy hollow fiber bundle is virtually homogeneous and tends to be similar to that of the blood temperature, which in turn tends to be similar to the heat-exchange fluid temperature. Therefore, within most of the oxy bundle, water vapor contained in gas and extracted with $CO_2$ from blood through fiber microporosity is not likely to condense, as there is generally is virtually no difference in temperature between gas and blood. However, gas temperature often significantly decreases towards the gas outlet end of the gas exchanger, where the fibers come into contact with a potting volume (at temperature lower than gas), which acts like a cooling element and causes water vapor condensation inside the fibers.

Embodiments of the subject matter disclosed herein facilitate reducing this temperature difference and, in turn, reducing the occurrence of condensation within the gas-exchange fibers. In embodiments, an insulator is disposed adjacent the gas outlet end of the gas exchanger. The insulator may include an insulating chamber that is disposed adjacent the gas outlet end of the gas exchanger (and, in some cases, at least a portion of the oxygenator housing), and is configured to receive an insulating fluid, which may, in embodiments, be a portion of a heat-exchange fluid flow. In embodiments, the insulator may include an insulating material that may be applied to an external surface of the oxygenator housing. Embodiments may include both an insulating chamber and an insulating material.

The disclosure pertains to a blood processing apparatus that, according to various embodiments, includes a gas exchanger (also commonly referred to as an oxygenator) and, in embodiments, also a heat exchanger. In embodiments, the term "oxygenator" may be used to refer to a blood processing apparatus configured to perform a gas exchange process such as, for example, a stand-alone gas exchanger or an integrated structure that combines a gas exchanger with another system (e.g., a heat exchanger) in a unitary device. In embodiments, for example, a heat exchanger and a gas exchanger are disposed in a concentric fashion with one component located inside of the other component. According to other embodiments, the heat exchanger and gas exchanger are structurally distinct structures operable coupled to each other. In embodiments, an oxygenator may be used in an extracorporeal blood circuit. An extracorporeal blood circuit, such as may be used in a bypass procedure, may include several different elements such as a heart-lung machine, a blood reservoir, as well as an oxygenator. Oxygenators may also be used in procedures such as extracorporeal membrane oxygenation (ECMO), and/or the like.

FIG. 1 is a schematic illustration of an oxygenator 100. The oxygenator 100 may include a gas exchanger and, in embodiments, a heat exchanger. In embodiments, the oxygenator 100 may include any number of other devices such as, for example, a blood filter, a blood pump, and/or the like. According to embodiments, a heat exchanger and a gas exchanger may be integrated within the oxygenator 100. The oxygenator 100 includes a housing 102, a first end cap 104 that is secured to a first end 106 of the housing 102 and a second end cap 108 that is secured to a second end 110 the housing 102. In embodiments, the first end cap 104 and/or the second end cap 108 may be adhesively secured in place. In embodiments, the first end cap 104 and/or the second end cap 108 may be snap-fitted into place, threaded onto their respective ends of the housing 102, and/or the like.

In embodiments, the housing 102 may include structures that enable attachment of the housing 102 to other devices. While the housing 102 is illustrated as generally cylindrical in shape, in embodiments, the housing 102 may have any number of different shapes (e.g. rectangular or other parallelogram cross-sectional shapes, oblong cross-sectional shapes, etc.). In embodiments in which the oxygenator 100 includes a heat exchanger and a gas exchanger, each of the heat exchanger and the gas exchanger may have approximately the same cross-sectional shape or each may have a different cross-sectional shape. In embodiments, the heat exchanger may be inside the gas exchanger. In embodiments, the heat exchanger and the gas exchanger may be concentric.

In embodiments, a blood inlet 112 extends into the housing 102 and a blood outlet 114 exits the housing 102. The illustrated oxygenator 100 includes a gas-exchange fluid inlet 116 configured to facilitate providing a gas-exchange fluid (such as air, oxygen, a mixture of oxygen and other gases, and/or the like) to the oxygenator 100, a gas-exchange fluid outlet 118 configured to facilitate removing a gas-exchange fluid from the oxygenator 100, a heat-exchange fluid inlet 120 configured to facilitate providing a heat-exchange fluid such as water to the oxygenator 100, and a heat-exchange fluid outlet 122 configured to facilitate removing a heat-exchange fluid from the oxygenator 100 and, for example, that, in the illustrated embodiment, is behind the heat-exchange fluid inlet 120. In embodiments, the heat-exchange fluid inlet 120 may be disposed at one end of the housing 102 while the heat-exchange fluid outlet 122 may be disposed at an opposite end of the housing 102. The heat-exchange fluid inlet 120 is configured to facilitate providing heat-exchange fluid to a heat exchanger disposed within the housing 102. Additionally, in embodiments, the heat-exchange fluid inlet 120 may be configured to facilitate providing heat-exchange fluid to an insulating chamber 124 disposed adjacent a gas-exchange fluid outlet region to facilitate reducing a temperature gradient between blood and gas exiting the oxygenator 100. In embodiments, the oxygenator 100 may include a separate heat-exchange fluid inlet coupled to the insulating chamber 124. In embodiments, the oxygenator 100 may include a conduit disposed outside or inside the housing 102 that facilitates transporting a portion of the heat-exchange fluid from the heat exchanger to the insulating chamber 124 and/or from the insulating chamber 124 to the heat exchanger. In this manner, embodiments of the subject matter disclosed herein may be configured to facilitate reduction of condensation within the gas exchanger.

In embodiments, the blood inlet 112 and/or the gas-exchange fluid inlet 116 may be integrally formed with the first end cap 104. For example, in some cases, the first end cap 104 may be injection molded with the blood inlet 112 and/or the gas-exchange fluid inlet 116 formed as part of the injection molded part. In embodiments, the first end cap 104 may be formed having apertures to which the blood inlet 112 and/or the gas-exchange fluid inlet 116 may be coupled. Similarly, in embodiments, the heat-exchange fluid inlet 120 and/or the heat-exchange fluid outlet 122 may be integrally formed with the second end cap 108. For example, in some cases, the second end cap 108 may be injection molded with the heat-exchange fluid inlet 120 and/or the heat-exchange fluid outlet 122 formed as part of the injection molded part. Similarly, in embodiments, the second end cap 108 may be injection molded with the gas-exchange fluid outlet 118 formed as part of the injection-molded part. In embodiments, the second end cap 108 may be formed having apertures to which one or more of the heat-exchange fluid inlet 120, the heat-exchange fluid outlet 122 and/or the gas-exchange fluid outlet 118 may be coupled. In embodiments, one of the heat-exchange fluid inlet 120 and the heat-exchange fluid outlet 122 may be located in the first end cap 104 while the other of the heat-exchange fluid inlet 120 and the heat-exchange fluid outlet 122 may be located in the second end cap 108. In embodiments, the heat-exchange fluid inlet 120 and outlet 122 may be located in the first end cap 104, while in other embodiments, the heat-exchange fluid inlet 120 and outlet 122 may be located in the second end cap 108.

In embodiments, the oxygenator may include a purge port 126 that may be used for purging air bubbles from the interior of the oxygenator. The purge port 126 may be configured to permit gases (e.g., air bubbles) mixed with the exiting blood to be vented or aspirated and removed from the oxygenator 100. The positions, with respect to the housing 102 of the inlets, outlets and purge port are merely illustrative, as other arrangements and configurations are contemplated.

According to embodiments, the oxygenator 100 may include an insulating material disposed on the housing 102 configured to reduce heat dispersion from the oxygenator 100 to the environment. The insulating material may be employed in lieu of, or in addition to, an insulating chamber. The term "insulator" may refer to insulating material and/or an insulating chamber. According to embodiments, any number of different types of insulating materials may be provided on, or in, the housing 102, and, in embodiments, a number of insulating materials may be used simultaneously. In embodiments, the insulating materials may include, for example, transparent (or at least partially transparent) coatings or paints with low thermal conductivity such as, for example, BASF Top Coat 603 Full White, Clear Coat Tixo Opaque 10 Gloss GP31-0436, and/or the like.

In embodiments, the insulating material may be removeably or permanently fixed to an outer surface of the housing 102 and/or an inner surface of the housing 102. For example, in embodiments, the insulating material may include one or more blankets wrapped around at least a portion of the housing 102. The blanket(s) may be secured in place by folding, tying, or otherwise manipulating the blanket; using an adhesive; using a mechanical fastener (e.g., a snap, clip, etc.); and/or the like. In embodiments, insulating blankets may be made of neoprene, aluminum foil, and/or the like. According to embodiments, the insulating material may be an insulating adhesive such as, for example, an insulating tape 128 that is wrapped around at least a portion of the outer surface of the housing. For example, a strip of insulating tape 128 may be wrapped around the end of the housing 102 adjacent a gas outlet end of the bundle of gas-exchange fibers. By applying an insulating material to the oxygenator housing 102, heat dispersion from the device to the environment may be reduced, thus decreasing the blood/gas temperature gradient and, in turn, inhibiting condensation within the gas-exchange fibers.

The illustrative oxygenator 100 shown in FIG. 1 is not intended to suggest any limitation as to the scope of use or functionality of embodiments of the present disclosure. The illustrative oxygenator 100 should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2:
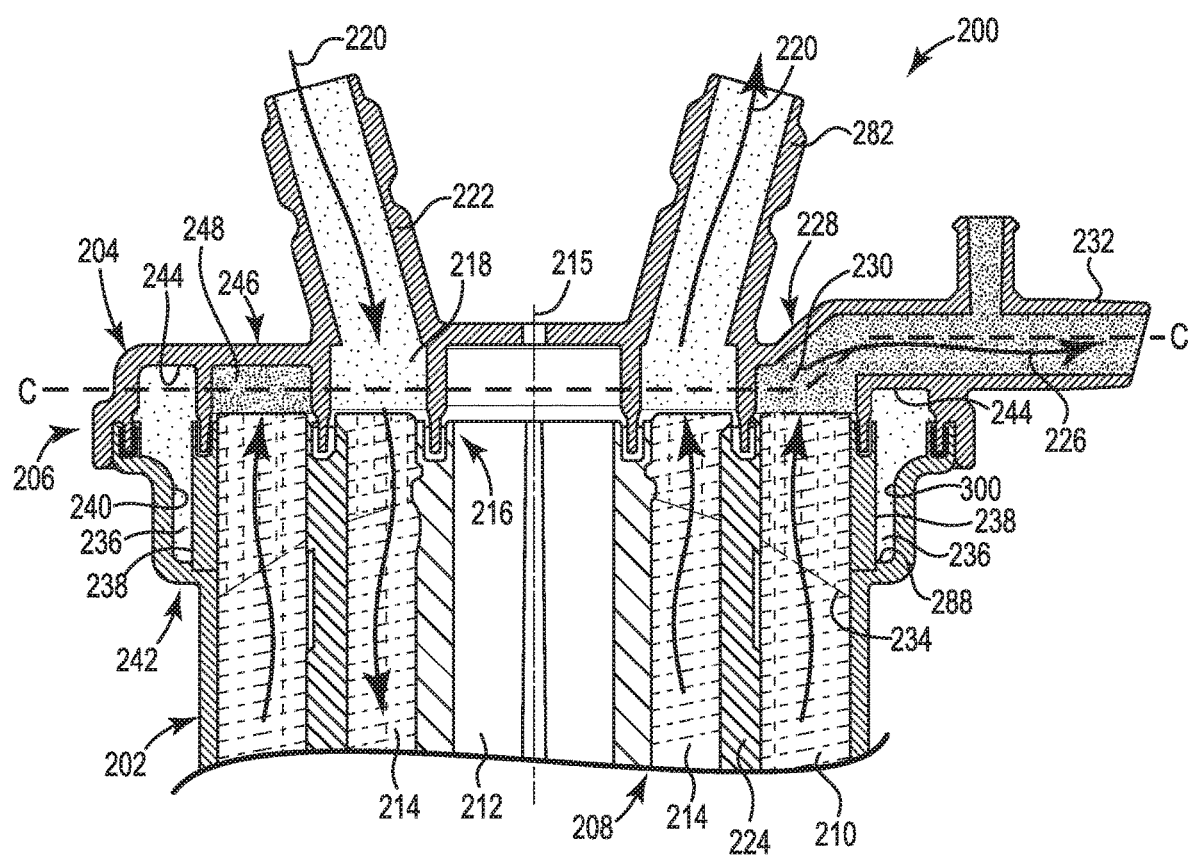
FIG. 2 is a partial cross-sectional side view of an illustrative oxygenator, taken along line B-B depicted in FIG. 3, in accordance with embodiments of the disclosed subject matter.
Figure 3:
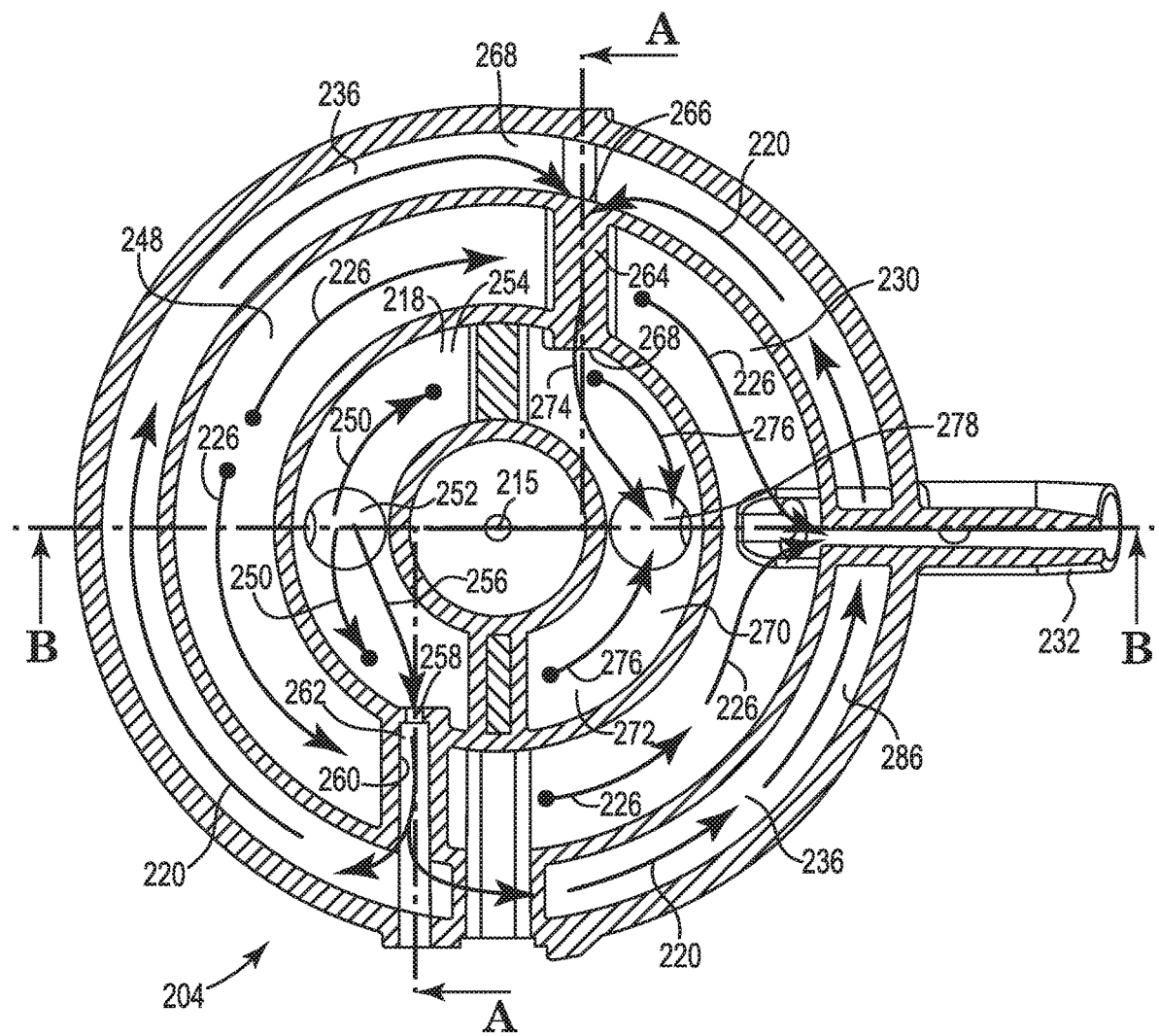
FIG. 3 is a cross-sectional view of an end cap of the illustrative oxygenator depicted in FIG. 2, in accordance with embodiments of the disclosed subject matter.
Figure 4:
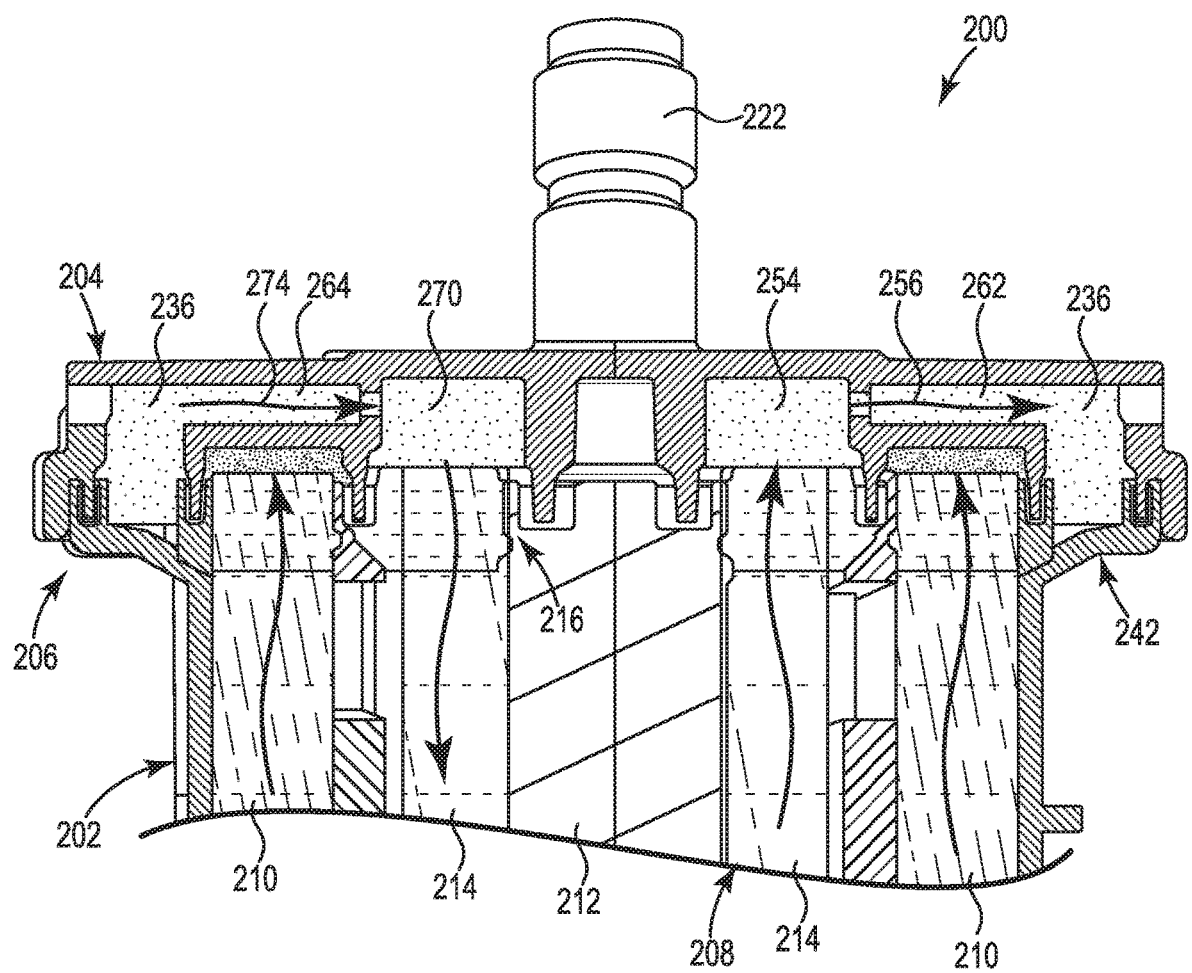
FIG. 4 is another partial cross-sectional side view of the illustrative oxygenator depicted in FIGS. 2 and 3, taken along line A-A depicted in FIG. 3, in accordance with embodiments of the disclosed subject matter.

FIGS. 2-4 depict an illustrative oxygenator 200 having a thermally-insulating chamber, according to embodiments of the disclosed subject matter. FIG. 2 is a partial cross-sectional side view of the oxygenator 200, taken along B-B depicted in FIG. 3; FIG. 3 is a cross-sectional view of a second end cap, taken along C-C, of the oxygenator 200 depicted in FIG. 2; and FIG. 4 is another cross-sectional side view of the oxygenator 200, taken along A-A, shown in FIG. 3. In embodiments, the oxygenator 200 may be, be similar to, include, or be included within the oxygenator 100 depicted in FIG. 1.

The oxygenator 200 includes a housing 202 having a first end cap (not shown) coupled to a first end (not shown) of the housing 202 and a second end cap 204 coupled to the second end 206 of the housing 202. As shown, the illustrative oxygenator 200 includes a heat exchanger 208 and a gas exchanger 210. The heat exchanger 208 includes a heat-exchanger core 212 and a heat-exchanger element 214 coaxially disposed about the heat-exchanger core 212. According to various embodiments, the heat-exchanger core 212 may have any number of different types of configurations and/or may include any number of features configured for imparting a desired blood flow through the oxygenator 200. For example, the heat-exchanger core 212 may include rib features, indentions, and/or the like.

In embodiments, the heat-exchanger element 214 may include a number of hollow fibers through which a heat-exchange fluid such as water can flow. The fibers of the heat-exchanger element 214 are bundled and the bundle is coupled, at an inlet end 216 thereof, to a heat-exchange fluid inlet channel 218, which is configured to allow an incoming heat-exchange fluid 220 to flow from a heat-exchange fluid inlet 222 to the bundle of fibers. The blood may flow around and past the hollow fibers and thus be suitably heated. According to various embodiments, the hollow fibers may have an outer diameter of between approximately 0.2 and approximately 1.0 millimeters or, more specifically, between approximately 0.25 and approximately 0.5 millimeters. The hollow fibers may be woven into mats that can range, for example, from approximately 20 to approximately 200 millimeters in width. In embodiments, the mats are arranged in a criss-cross configuration. According to embodiments, the heat-exchanger element 214 may include a number of pleated thin metal surfaces (e.g., an array of metal plates, sheets, etc.). The heat-exchanger element 214 may include any number of other types of heat-exchange media and/or structures.

A cylindrical shell 224 is coaxially disposed about the heat-exchanger element 214, and the gas exchanger 210 is coaxially disposed about the cylindrical shell 224. For reference, as depicted in the figures, the cylindrical shell 224 and gas exchanger 210 may share a vertical central axis 215. In embodiments, the gas exchanger 210 may include a number of microporous hollow gas-exchange fibers through which a gas-exchange fluid 226 (e.g., a gas such as oxygen, a mix of oxygen and one or more other gases, air, etc.) may flow. The fibers of the gas exchanger 210 are bundled and the bundle is coupled, at an inlet end (not shown) thereof to an inlet flow coupler (not shown), which is configured to provide an incoming gas-exchange fluid 226 from a gas-exchange fluid inlet (not shown) to the bundle of fibers. Similarly, the bundle of gas-exchange fibers may be coupled, at a gas outlet end 228 to a gas-exchange fluid outlet channel 230, which is configured to provide the gas-exchange fluid 226 from the bundle to a gas-exchange fluid outlet 232. The blood may flow around and past the hollow fibers. Due to concentration gradients, oxygen may diffuse through the microporous hollow fibers into the blood while carbon dioxide may diffuse into the hollow fibers and out of the blood. In embodiments, the hollow fibers may be made of polypropylene, polyester, or any other suitable polymer or plastic microporous and hydrophobic materials. According to various embodiments, the hollow fibers have an outer diameter of approximately 0.38 millimeters. According to embodiments, the microporous hollow fibers may have a diameter of between approximately 0.2 and approximately 1.0 millimeters, or more specifically, between approximately 0.25 and approximately 0.5 millimeters. The hollow fibers may be woven into mats that can range, for example, from approximately 20 to approximately 200 millimeters in width. In embodiments, the mats are arranged in a criss-cross configuration.

According to embodiments, the ends of the gas-exchange fibers and/or heat-exchange fibers or metal surfaces may be embedded within a potting material (e.g., a potting resin) 234 adjacent the end cap 204. In embodiments, an insulating chamber 236 may be defined between a first portion 238 of the inner surface of a flange 242 at the second end 206 of the housing 202, a second portion 240 of the inner surface of the flange 242, and an inner surface 244 of the end cap 204. In embodiments, the flange 242 may be integrated with the housing 202, in which case, the flange 242 may be considered to be a part of the housing 202. In embodiments, the flange 242 may be, for example, separately constructed and coupled to the housing.

The insulating chamber 236 may be disposed adjacent a gas outlet end 246, a gas-exchange transition channel 248 of the gas exchanger 208, and the gas-exchange fluid outlet channel 230. The insulating chamber 236 may be configured to receive an insulating fluid that facilitates maintaining the gas-exchange fluid 226 at (or approximately) a certain temperature or approximately within a certain temperature range. This temperature and/or temperature range may be selected so as to reduce the occurrence of condensation within the gas-exchange fibers. In embodiments, as shown, the insulating chamber 236 may include an annular (or at least partially annular) chamber, extending coaxially around at least a portion of the gas outlet end 246 of the gas exchanger 208. In this case, the gas-exchange transition channel 248 may be a part of the fluid outlet channel 230.

In embodiments, the insulating chamber 236 may be designed according to any number of different shapes and to have any number of different positions. In embodiments, the insulating chamber 236 may be a number of different chambers (e.g., semi-annular chambers), and, in embodiments, two or more of those chambers may be connected so as to allow for insulating fluid to move between them. In embodiments, the insulating chamber 236 may be configured to surround a portion of the end cap 204, the entire end cap 204, a portion of the housing 202, the entire housing 202, and/or the like. The insulating chamber 236 may be configured to have a constant depth (i.e., the distance between the end of the chamber 236 bounded by the inner surface 244 of the end cap 204 and the opposing portion 288 of the inner surface 240); and/or width (i.e., the distance between the surface 238 and the opposing portion 300 of the inner surface 240 of the flange 242). In embodiments, for example, the flange 242 may include a curved configuration providing a varying volume adjacent the housing 202.

In embodiments, the insulating fluid may be the same as the heat-exchange fluid 220, while, in other embodiments, the insulating fluid may be a different type of fluid. In embodiments in which the insulating fluid is different than the heat-exchange fluid, the oxygenator 200 may include an insulating fluid inlet (not shown) and/or an insulating fluid outlet (not shown), configured to facilitate circulation of the insulating fluid into and out of the oxygenator. In embodiments, a heating device (not shown) may be provided for modifying (e.g., increasing) the temperature of the insulating fluid before it is provided to the oxygenator 200.

In embodiments in which the insulating fluid is the same as the heat-exchange fluid 220 of the heat exchanger 208, a first portion of the flow of heat-exchange fluid 220 being provided to the oxygenator 200 may be provided to the heat exchanger 208, while a second portion of the heat-exchange fluid 220 being provided to the oxygenator 200 may be provided to the insulating chamber 236. That is, for example, the heat-exchange fluid inlet channel 218 may be configured to enable a first portion 250 of the incoming heat-exchange fluid 220 flowing from the heat-exchange fluid inlet 222 into the heat-exchange fluid inlet channel 218, via an aperture 252 defined in an inner wall surface 254 bounding the heat-exchange fluid inlet channel 218, to flow to the heat exchanger 208, and a second portion 256 of the incoming heat-exchange fluid 220 to flow, via an aperture 258 extending from the inner wall surface 254 bounding the heat-exchange fluid inlet channel 218 to an inner wall surface 260 bounding a first connecting channel 262, through the first connecting channel 262 into the insulating chamber 236. In this manner, a fresh supply of heat-exchange fluid 220 may be continuously (or continually) moved through the insulating chamber 236.

A second connecting channel 264 extends from an aperture 266 defined in the inner surface 244 of the end cap 204 to an aperture 268 defined in an inner wall surface 270 bounding a heat-exchange fluid outlet channel 272. The portion 274 of heat-exchange fluid flowing into the heat-exchange fluid outlet channel 272 from the insulating chamber 236 joins a portion 276 of fluid exiting the heat exchanger 208 to flow, via an aperture 278 defined in the inner wall surface 270, to a heat-exchange outlet 282. As shown in FIG. 3, the connecting channels 262 and 264 may be arranged offset from one another as indicated by lines A-A. In other embodiments, the connecting channels 262 and 264 may be in line with one another. The connecting channels 262 and 264 may be configured to have a certain size (e.g., diameter) that, coupled with a certain heat-exchange fluid flow rate into the oxygenator, imparts a certain flow rate to the portion of the heat-exchange fluid that flows into the insulating chamber 236. In this manner, for example, different fluid flow rates associated with the insulating chamber 236 may be selected by substituting different end caps, each having connecting channels, inlet channels, and/or outlet channels sized to impart corresponding flow rates, thus influencing the blood/gas temperature gradient.

As shown in FIGS. 2-4, the insulating chamber 236 surrounds the gas outlet end 246 of the gas exchanger 210, as well as the gas-exchange fluid outlet channel 230 and the gas-exchange transition channel 248. As is illustrated, the insulating chamber 236; the channels 218, 230, 272, 248; and the connecting channels 262 and 264 may be defined in an inner surface 286 of the end cap 204. For example, in embodiments, the end cap may be manufactured to include any one or more of the features 218, 230, 236, 262, 264, 272, and 248. In other embodiments, one or more of the insulating chamber 236; the channels 218, 230, 272, 248; and the connecting channels 262 and 264 may be defined within one or more portions of the housing 202, defined by a combination of one or more portions of the housing 202 and one or more portions of the inner surface 286 of the end cap 204, defined within an insert (like the flange 242) configured to be disposed between the end cap 204 and the housing 202 (and/or the heat exchanger 208, the gas exchanger, etc.), and/or the like.

The illustrative oxygenator 200 shown in FIGS. 2-4 is not intended to suggest any limitation as to the scope of use or functionality of embodiments of the present disclosure. The illustrative oxygenator 200 should not be interpreted as having any dependency or requirement related to any single component or combination of components illustrated therein. Additionally, various components depicted in FIGS. 2-4 may be, in embodiments, integrated with various ones of the other components depicted therein (and/or components not illustrated), all of which are considered to be within the ambit of the present disclosure.

Figure 5:
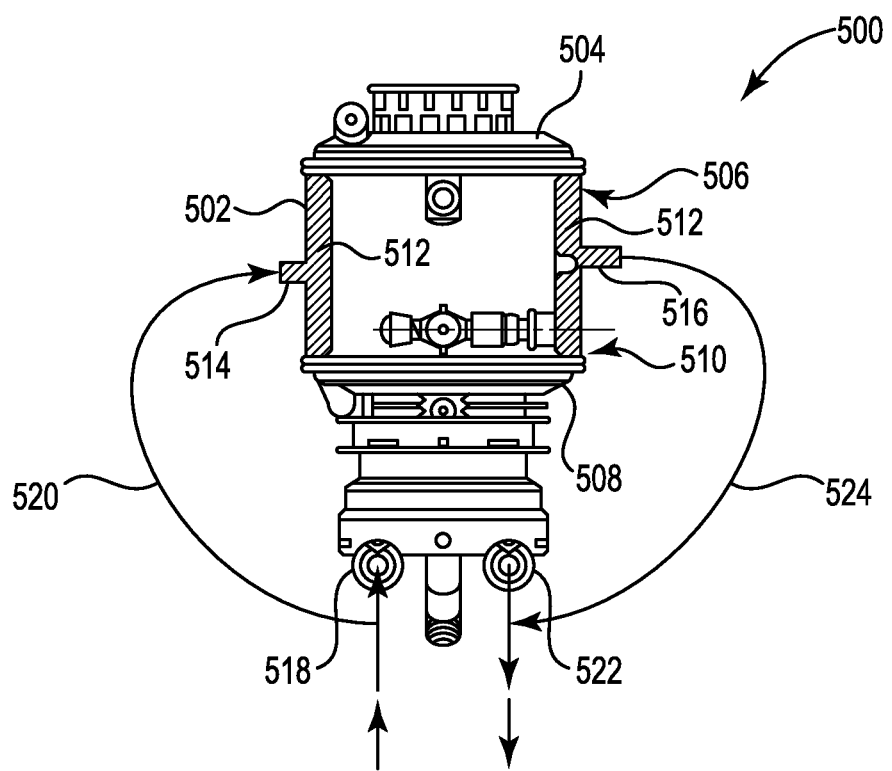
FIG. 5 is a schematic diagram of an illustrative oxygenator, in accordance with embodiments of the disclosed subject matter.

As explained above, embodiments may include an oxygenator having an insulating chamber disposed around at least a portion of the housing of the oxygenator. This may be particularly true, e.g., in the case of small CPB or ECMO oxygenators. FIG. 5 is a schematic depiction of an illustrative oxygenator having an insulating chamber, in accordance with embodiments of the disclosed subject matter.

FIG. 5 depicts an illustrative oxygenator 500 configured to be used in small CPB operations, in accordance with embodiments of the disclosed subject matter. According to embodiments, the oxygenator 500 may be, be similar to, include, be included in, or include similar features as the oxygenator 100 depicted in FIG. 1 and/or the oxygenator 200 depicted in FIGS. 2-4. As shown, the oxygenator 500 includes a housing 502, a first end cap 504 disposed at a first end 506 of the housing, and a second end cap 508 disposed at a second end 510 of the housing 502. An insulating chamber 512 is disposed around at least a portion of the housing 502. In embodiments, that is, the insulating chamber 512 may be coupled to an outer surface of the housing 502, while, in other embodiments, the insulating chamber 512 may be defined within the housing, e.g., just under the outer surface thereof. As illustrated, the insulating chamber 512 extends from the first end 506 of the housing 502 to the second end 510 of the housing 502. In other embodiments, the insulating chamber 512 only extends part of the way between the first and second ends 506 and 510 of the housing 502. Similarly, in embodiments, the insulating chamber 512 may be disposed circumferentially around (inside the housing 502 or outside the housing 502) the entire circumference of the housing 502, or may extend only partially around (inside the housing 502 or outside the housing 502) the circumference of the housing 502.

As shown in FIG. 5, the insulating chamber 512 includes an insulating-fluid inlet 514 configured to provide insulating fluid from an insulating-fluid source (e.g., a fluid heating device, a reservoir or a container, a heat exchanger, etc.), to the insulating chamber 512. The insulating chamber 512 also includes an insulating-fluid outlet 516 configured to facilitate removing insulating fluid from the insulating chamber 512. In embodiments, the insulating-fluid inlet 514 may be coupled to a heat-exchange fluid inlet 518 via a conduit 520 disposed within the oxygenator 500 and/or outside of the oxygenator 500. In embodiments, for example, a first inlet conduit (not shown) may extend from the heat-exchange fluid inlet 518 to a heat exchanger (not shown) disposed within the housing 502, and a second inlet conduit (not shown, but indicated conceptually at 520) may extend from the heat-exchange fluid inlet 518, or from the first inlet conduit, to the insulating-fluid inlet 514, which may be defined within the housing 502 and/or on the outside of the housing 502. Similarly, a first outlet conduit (not shown) may extend from the heat exchanger to a heat-exchange fluid outlet 522, and a second outlet conduit (not shown, but indicated conceptually at 524) may extend from the insulting-fluid outlet 516 (which may be disposed within the housing 502 and/or outside of the housing 502) to the heat-exchange fluid outlet 522, or to the first outlet conduit.

The illustrative oxygenator 500 shown in FIG. 5 is not intended to suggest any limitation as to the scope of use or functionality of embodiments of the present disclosure. The illustrative oxygenator 500 should not be interpreted as having any dependency or requirement related to any single component or combination of components illustrated therein. Additionally, various components depicted in FIG. 5 may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An oxygenator configured to oxygenate blood flowing therethrough, the oxygenator comprising:
   a housing having a blood inlet and a blood outlet, the blood inlet extending into an interior of the housing;
   a heat exchanger disposed within the housing, the heat exchanger coupled, at an inlet end, to a heat-exchange fluid inlet;
   a gas exchanger disposed within the housing, the gas exchanger comprising a bundle of gas-exchange fibers coupled, at a gas outlet end, to a gas- exchange fluid outlet, wherein the heat exchanger is disposed concentrically within the gas exchanger; and
   an insulating chamber configured to thermally insulate at least the gas outlet end of the bundle of gas-exchange fibers, wherein the insulating chamber is configured to receive a flowing insulating fluid different than the blood flowing through the oxygenator;
   wherein the gas outlet end of the bundle of gas-exchange fibers is embedded within a potting material;
   wherein at least a portion of the insulating chamber is disposed radially outward of the potting material upstream of the gas outlet end of the bundle of gas-exchange fibers.

2. The oxygenator of claim 1, further comprising an insulating material configured to thermally insulate at least the gas outlet end of the bundle of gas-exchange fibers, wherein the insulating material is transparent.

3. The oxygenator of claim 2, wherein the insulating material comprises at least one of a transparent paint and a transparent adhesive tape.

4. The oxygenator of claim 1, wherein the insulating fluid comprises a portion of a flow of heat-exchange fluid being provided to the oxygenator.

5. The oxygenator of claim 1, further comprising a conduit disposed outside of the oxygenator housing and configured to provide the insulating fluid to the insulating chamber.

6. The oxygenator of claim 1, wherein the insulating chamber surrounds at least a portion of the housing.

7. The oxygenator of claim 1, wherein the oxygenator further comprises a first end cap disposed at a first end of the housing, and a second end cap disposed at a second end of the housing, and wherein the insulating chamber is partially defined between an outer surface of the second end of the housing and an inner surface of the second end cap.

8. The oxygenator of claim 7, wherein the insulating chamber is at least partially defined by a channel defined in an inner surface of the second end cap.

9. The oxygenator of claim 8, further comprising a connecting channel defined in the inner surface of the second end cap, the connecting channel extending between a heat-exchange fluid inlet channel and the insulating chamber.

10. The oxygenator of claim 9, further comprising an additional connecting channel defined in the inner surface of the second end cap, the additional connecting channel extending between the insulating chamber and a heat-exchange fluid outlet channel.

11. The oxygenator of claim 10, wherein the connecting channel and additional connecting channel are offset from one another.

12. An oxygenator comprising:
   a housing having a blood inlet and a blood outlet, the blood inlet extending into an interior of the housing;
   a heat exchanger disposed within the housing, the heat exchanger coupled, at an inlet end, to a heat-exchange fluid inlet;
   a gas exchanger disposed within the housing, the gas exchanger comprising a bundle of gas-exchange fibers coupled, at a gas outlet end, to a gas- exchange fluid outlet; and
   an insulating chamber configured to receive a flowing insulating fluid to thermally insulate at least the gas outlet end of the bundle of gas-exchange fibers;
   wherein the gas outlet end of the bundle of gas-exchange fibers is embedded within a potting material;
   wherein at least a portion of the insulating chamber circumferentially surrounds a radially outermost surface of the potting material.

13. The oxygenator of claim 12, the oxygenator further comprising a first end cap disposed at a first end of the housing, and a second end cap disposed at a second end of the housing, wherein the insulating chamber is bounded by the inner surfaces of a flange extending from the housing at the second end of the housing, and an inner surface of the second end cap.

14. The oxygenator of claim 12, wherein the insulating chamber comprises an annular chamber extending at least partially around the gas outlet end of the gas exchanger.

15. The oxygenator of claim 12, wherein the insulating fluid comprises a portion of a flow of heat-exchange fluid being provided to the oxygenator.

16. The oxygenator of claim 12, further comprising an insulating material disposed on an outer surface of the housing.

17. An oxygenator comprising:

a housing having a blood inlet and a blood outlet, the blood inlet extending into an interior of the housing;

a first end cap disposed at a first end of the housing;

a second end cap disposed at a second end of the housing;

a heat exchanger disposed within the housing, the heat exchanger coupled, at an inlet end, to a heat-exchange fluid inlet;

a gas exchanger disposed within the housing, the gas exchanger comprising a bundle of gas-exchange fibers coupled, at a gas outlet end, to a gas- exchange fluid outlet; and an insulating chamber configured to receive a flowing insulating fluid to thermally insulate at least the gas outlet end of the bundle of gas-exchange fibers, wherein the insulating chamber is at least partially defined by a fluid channel defined in an inner surface of the second end cap;

wherein at least a portion of the insulating chamber extends toward the first end of the housing from the gas outlet end of the bundle of gas-exchange fibers.

18. The oxygenator of claim 17, wherein the insulating fluid comprises a portion of a flow of heat-exchange fluid being provided to the oxygenator.

19. The oxygenator of claim 17, further comprising an insulating material disposed on an outer surface of the housing.

* * * * *